(12) United States Patent
Smith

(10) Patent No.: US 12,018,859 B2
(45) Date of Patent: Jun. 25, 2024

(54) SCALABLE OZONE GENERATOR SYSTEMS AND METHODS FOR RETROFIT OF DUCTED HVAC SYSTEMS

(71) Applicant: Quail Systems, LLC, Adamsville, TN (US)

(72) Inventor: Robert W. Smith, Adamsville, TN (US)

(73) Assignee: Tennessee Innovative Products, LLC, Adamsville, TN (US)

( * ) Notice: Subject to any disclaimer, the term of this patent is extended or adjusted under 35 U.S.C. 154(b) by 0 days.

(21) Appl. No.: 17/837,070

(22) Filed: Jun. 10, 2022

(65) Prior Publication Data

US 2022/0397293 A1 Dec. 15, 2022

Related U.S. Application Data

(60) Provisional application No. 63/210,562, filed on Jun. 15, 2021.

(51) Int. Cl.
*F24F 8/26* (2021.01)
*A61L 2/20* (2006.01)
(Continued)

(52) U.S. Cl.
CPC ............... *F24F 8/26* (2021.01); *A61L 2/202* (2013.01); *A61L 2/24* (2013.01); *A61L 2202/11* (2013.01);
(Continued)

(58) Field of Classification Search
CPC ...... F24F 8/26; F24F 2120/10; F24F 2110/74; F24F 2221/22; F24F 13/20; A61L 2/202;
(Continued)

(56) References Cited

U.S. PATENT DOCUMENTS 4,849,237 A 7/1989 Hurst
5,956,562 A 9/1999 Lo et al.
(Continued)

FOREIGN PATENT DOCUMENTS

CA 2450117 A1 12/2002
CA 2473540 A1 7/2003
(Continued)

OTHER PUBLICATIONS

Web Reference , "ZoneAir Products; Commercial Air Purifier Solutions", https://www.zoneair.com/commercial-air-purifier/ Printed: Aug. 16, 2022, 12:16 pm, Aug. 16, 2022, 10 Pages.

*Primary Examiner* — Xiuyu Tai
(74) *Attorney, Agent, or Firm* — Blanchard Horton PLLC

(57) ABSTRACT

An HVAC duct ozone generator includes at least two ozone generation plate stacks, where each plate stack includes at least two independently electrically addressable plate groupings, where a primary plate grouping includes fewer ozone generation plates than a secondary plate grouping. Thus, the generator includes at least four independent ozone generation control channels to energize the primary and secondary plate groupings of each of the at least two plate stacks. The number of plates in a plate grouping may optionally be altered to reduce the ozone generation capacity of the primary plate grouping in relation to the secondary plate grouping through the movement of insulators between the stacked ozone generation plates.

25 Claims, 4 Drawing Sheets

(51) Int. Cl.
   *A61L 2/24* (2006.01)
   *F24F 110/74* (2018.01)
   *F24F 120/10* (2018.01)

(52) U.S. Cl.
   CPC ....... *A61L 2202/14* (2013.01); *A61L 2202/25* (2013.01); *F24F 2110/74* (2018.01); *F24F 2120/10* (2018.01); *F24F 2221/22* (2013.01)

(58) Field of Classification Search
   CPC .... A61L 2/24; A61L 2202/11; A61L 2202/14; A61L 2202/25; A61L 9/046; A61L 9/12; A61L 2209/15; A61L 2209/16; A61L 2101/02; A61L 2209/212; A61L 2209/111; B01J 19/08; B01J 19/088; C01B 13/10; C01B 13/11; C01B 13/115; C01B 2201/40; C01B 2201/12; C01B 2201/76; C01B 2201/90; C01B 2201/84; C01B 2201/32; C01B 2201/24; Y02A 50/20; H02M 7/48
   See application file for complete search history.

(56) References Cited

U.S. PATENT DOCUMENTS

| | | |
|---|---|---|
| 6,589,480 B1 | 7/2003 | Yuan et al. |
| 6,669,902 B1 | 12/2003 | Steiner et al. |
| 6,893,610 B1 | 5/2005 | Barnes |
| 7,407,624 B2 | 8/2008 | Cumberland et al. |
| 7,425,301 B2 | 9/2008 | Gillette et al. |
| 7,614,260 B2 | 11/2009 | Daniels et al. |
| 8,020,232 B2 | 9/2011 | Daniels et al. |
| 8,056,358 B1 | 11/2011 | Shelton |
| 8,211,374 B2 | 7/2012 | Hallam |
| 8,226,899 B2 | 7/2012 | Woodbridge |
| 8,551,399 B2 | 10/2013 | Shannon et al. |
| 8,636,951 B2 | 1/2014 | Shannon et al. |
| 8,754,385 B1 | 6/2014 | Gutman |
| 8,984,914 B2 | 3/2015 | Daniels et al. |
| 8,992,829 B2 | 3/2015 | Shannon et al. |
| 9,034,251 B1 | 5/2015 | Gutman |
| 9,375,500 B2 | 6/2016 | Dunkley et al. |
| 9,616,144 B2 | 4/2017 | Shannon et al. |
| 9,657,423 B2 | 5/2017 | Daniels et al. |
| 10,342,246 B2 | 7/2019 | Smith |
| 10,555,548 B2 | 2/2020 | Smith |
| 2003/0039729 A1 | 2/2003 | Murphy et al. |
| 2003/0071069 A1 | 4/2003 | Shelton |
| 2003/0156978 A1 | 8/2003 | Gillette et al. |
| 2004/0003511 A1 | 1/2004 | Silver |
| 2005/0011372 A1 | 1/2005 | Corrigan et al. |
| 2005/0129571 A1 | 6/2005 | Centanni |
| 2006/0104858 A1 | 5/2006 | Potember et al. |
| 2006/0263276 A1 | 11/2006 | Pattee |
| 2006/0273186 A1 | 12/2006 | Corrigan et al. |
| 2007/0086914 A1 | 4/2007 | Antinozzi |
| 2007/0134140 A1* | 6/2007 | Tabata ................. C01B 13/115 422/186.07 |
| 2007/0217987 A1 | 9/2007 | Belanger et al. |
| 2008/0031770 A1 | 2/2008 | Heselton et al. |
| 2008/0092745 A1 | 4/2008 | Tsao et al. |
| 2008/0159910 A1 | 7/2008 | Dick et al. |
| 2008/0213125 A1 | 9/2008 | Boast et al. |
| 2008/0227680 A1 | 9/2008 | Lynn |
| 2009/0120473 A1 | 5/2009 | Lynn |
| 2009/0233839 A1 | 9/2009 | Lynn |
| 2010/0107343 A1 | 5/2010 | Daniels et al. |
| 2010/0126340 A1 | 5/2010 | Peterson |
| 2012/0020832 A1 | 1/2012 | St. Onge et al. |
| 2012/0063949 A1 | 3/2012 | Jennings |
| 2012/0100037 A1 | 4/2012 | Shannon et al. |
| 2012/0142575 A1 | 6/2012 | Lynn |
| 2014/0033445 A1 | 2/2014 | Daniels et al. |
| 2014/0037499 A1 | 2/2014 | Shannon et al. |
| 2014/0302168 A1 | 10/2014 | Perry |
| 2015/0329225 A1 | 11/2015 | Moncayo, Jr. |
| 2015/0343336 A1 | 12/2015 | Pett et al. |
| 2018/0070616 A1 | 3/2018 | Smith |
| 2018/0304226 A1 | 10/2018 | Khoshbin et al. |
| 2019/0143349 A1 | 5/2019 | Lewis et al. |
| 2019/0335790 A1 | 11/2019 | Smith |
| 2021/0114872 A1* | 4/2021 | Dempster ............. C01B 13/115 |
| 2021/0222898 A1* | 7/2021 | Verish ...................... F24F 8/26 |
| 2022/0152262 A1 | 5/2022 | Smith |

FOREIGN PATENT DOCUMENTS

| | | |
|---|---|---|
| CA | 2486831 A1 | 2/2004 |
| CA | 2491781 A1 | 7/2005 |
| CA | 2602230 A1 | 9/2005 |
| CA | 2526367 A1 | 4/2007 |
| CA | 2534700 A1 | 7/2007 |
| CA | 2641046 A1 | 8/2007 |
| CA | 2450117 C | 4/2011 |
| CN | 1537638 A | 10/2004 |
| CN | 201704063 U | 1/2011 |
| CN | 102908639 A | 2/2013 |
| CN | 202738766 U | 2/2013 |
| CN | 104233706 A | 12/2014 |
| CN | 205045923 U | 2/2016 |
| CN | 111265694 A | 6/2020 |
| EP | 1968653 B1 | 2/2013 |
| EP | 1973578 B1 | 3/2013 |
| GB | 2468519 A | 9/2010 |
| GB | 2468519 B | 1/2014 |
| GB | 2468520 B | 1/2014 |
| KR | 200200575 Y1 | 10/2000 |
| KR | 101291844 B1 | 8/2013 |
| WO | 9938374 A1 | 8/1999 |
| WO | 2004011041 A2 | 2/2004 |
| WO | 2005060385 A2 | 7/2005 |
| WO | 2005087278 A1 | 9/2005 |
| WO | 2009046562 A2 | 4/2009 |
| WO | 2011085466 A1 | 7/2011 |
| WO | 2012037678 A1 | 3/2012 |
| WO | 2013112197 A1 | 8/2013 |
| WO | 2016157383 A1 | 10/2016 |

* cited by examiner

SCALABLE OZONE GENERATOR SYSTEMS AND METHODS FOR RETROFIT OF DUCTED HVAC SYSTEMS

REFERENCE TO RELATED APPLICATIONS

This application claims the benefit of U.S. Provisional Application No. 63/210,562 entitled "Scalable Ozone Generator Systems and Methods for Retrofit of Ducted HVAC Systems" filed Jun. 15, 2021, which is incorporated by reference in its entirety.

BACKGROUND

Heating, Ventilating, and Air Conditioning (HVAC) systems are commonly used to control the air quality and provide comfortable temperatures in living spaces. HVAC systems may operate when living spaces are occupied or unoccupied by people and pets. HVAC systems generally include ducts and a HVAC temperature modification unit. HVAC ducts run throughout buildings and terminate with vents that provide airflow between the duct system and the living space. Ducts that transfer air from a living space to the HVAC temperature modification unit are often referred to as return ducts, while ducts than transfer air from the HVAC temperature modification unit to the living space are often referred to as supply ducts. HVAC temperature modification units often include a finned evaporator through which air is moved by one or more fans to alter the temperature of the air. During cooling, the evaporator is chilled by refrigerant to a lower temperature than the living space, while if so equipped, during heating the evaporator is heated by refrigerant to a higher temperature than the living space.

The ducts may be made from metal, plastic, fabric, other materials, and combinations of these materials, such as when the ducts are insulated. The HVAC temperature modification unit can heat, cool, or heat and cool air that is transferred from the living space into the return ducts, through the HVAC temperature modification unit, through the supply ducts, and then back into the living space. The HVAC temperature modification unit includes at least one fan to move the air from the return to the supply ducts. The HVAC temperature modification unit may provide air modification other than thermal, such filtration, humidification, dehumidification, and the like. The thermal modification components of the HVAC temperature modification unit generally include a vapor compression system that circulates refrigerant in a closed loop to transfer heat between the living space and an external medium. For example, during cooling the vapor compression system transfers heat from an interior living space to the air outside the building. Similarly, during heating, a heat pump vapor compression system transfers heat from the air outside the building to the interior living space.

HVAC ducts are a partially enclosed airspace inside the enclosed airspace within a building. As the interior of the ducts of the HVAC system is more enclosed than the building in which the system resides, the interior of the ducts is more susceptible to the growth and propagation of contaminants including molds, fungus, bacteria, virus, and other undesirable microorganisms. Once one or more of these contaminants begins to live in the HVAC system ducts, their spores, toxins, and the like are spread throughout the living space by the HVAC system fan or fans. Thus, when the fan is not running, an environment for the contaminants to propagate is provided, and when the fan turns on, the propagated contaminants are spread throughout the living space.

Contaminants that cannot readily propagate or concentrate in an open living space, often find a more hospitable growth environment within the HVAC system. A famous instance of this situation was when legionella bacteria established a colony within the HVAC system of a hotel and infected multiple guests, resulting in a serious form of atypical pneumonia that resulted in death. Without being concentrated prior to human inhalation, legionella bacteria generally do not cause severe sickness in humans. As with most toxic substances, dose per unit time is determinative of the degree of infection/illness. A similar situation exists with mold allergies, where small amounts of mold are relatively harmless, but after concentration in HVAC ducts, the resulting larger, concentrated amounts distributed in the living space by the HVAC system illicit an allergic response that may not be reversible depending on the concentration and length of exposure.

In addition to preventing the ducting of an HVAC system from becoming pathogenic or toxic, it is also beneficial to filter and potentially sanitize the air the passing through a HVAC system. An effective particulate filtration system provided in the return ducting can remove dust, pollen, mold spores, and some pathogens from the air in the living space before the unconditioned air passes through the HVAC temperature modification unit and before the air passes back into the living space. A sanitization system provided after the particulate filtration system has the potential to prevent contaminants not trapped by the particulate filtration system from reaching the HVAC temperature modification unit and the air of the living space.

By lowering the contaminant concentration of the air within the HVAC system and the living space, the incidence of disease transmission between the occupants of the living space can be significantly reduced. Similarly, if a sanitizing agent could be added to the air passing through the supply ducting and into the living space, in addition to additional elimination of airborne contaminants it could be possible to sanitize the surfaces of the living space, thus further reducing contaminant spread between room occupants. This would be especially beneficial in the context of pathogenic bacteria and viruses.

Ozone, an allotrope of oxygen, is an effective sanitizing agent of both air and surfaces. Ozone can directly oxidize harmful contaminants, thus rendering them harmless to humans, and can also oxidize undesirable contaminants that produce foul odors, thus rendering them odorless. Generally, ozone concentrations of 0.1 ppm in an enclosed airspace will destroy pathogens and eliminate most odors within 48 hours. Although conventional systems have attempted to use ozone as an effective sanitizing agent in combination with HVAC systems, there have been multiple disadvantages to such conventional systems.

One disadvantage of conventional ozone systems for HVAC use has been a difficulty in successfully retrofitting existing HVAC systems with the ozone sanitization system, often arising from the variability in enclosed airspace volumes. Another disadvantage has been the inability of conventional ozone systems to provide enough ozone to effectively control pathogen growth or to ensure that safe ozone levels for human occupancy were not exceeded. Another disadvantage of such conventional ozone systems, which are generally based on ultraviolet light generated ozone, is their relatively high failure rate in actual use.

As seen from the above description, there is an ongoing need for improved devices and methods for at least partially sanitizing the ducting systems of HVAC systems and the air that passes through such systems. The devices, methods, and systems of the present invention overcome at least one of the disadvantages associated with conventional HVAC system ozone systems.

SUMMARY

In one aspect, the invention provides a HVAC duct ozone generator, for reducing contamination of a HVAC system duct and associated living space including at least two ozone generator plate stacks comprising a first ozone generator plate stack and a second ozone generator plate stack, where the first ozone generator plate stack comprises at least two first plate stack independently electrically addressable plate groupings and the second ozone generator plate stack comprises at least two second plate stack independently electrically addressable plate groupings, where a primary plate grouping of the first plate stack comprises fewer ozone generator plates than a secondary plate grouping of the first plate stack, and where a primary plate grouping of the second plate stack comprises fewer ozone generator plates than a secondary plate grouping of the second plate stack.

In another aspect of the invention, there is a method of operating a HVAC system duct ozone generator within a HVAC system duct to reduce contamination of the HVAC system duct and associated living space including energizing a primary plate grouping of a first plate stack to attain an ozone concentration from 0.05 ppm to 0.08 ppm in an occupied living space; then de-energizing the primary plate grouping of the first plate stack; energizing a secondary plate grouping of a first plate stack to attain an ozone concentration from 2 ppm to 15 ppm in an unoccupied living space for 15 minutes to 2 hours; and then de-energizing the secondary plate grouping of the first plate stack Other systems, methods, features and advantages of the invention will be, or will become, apparent to one with skill in the art upon examination of the following figures and detailed description. It is intended that all such additional systems, methods, features, and advantages be included within this description, be within the scope of the invention, and be protected by the claims that follow. The scope of the present invention is defined solely by the appended claims and is not affected by the statements within this summary.

BRIEF DESCRIPTION OF THE FIGURES

The invention can be better understood with reference to the following drawings and description. The components in the figures are not necessarily to scale, emphasis instead being placed upon illustrating the principles of the invention.

DETAILED DESCRIPTION

An HVAC duct ozone generator includes at least two ozone generation plate stacks, where each plate stack includes at least two independently electrically addressable plate groupings, where a primary plate grouping includes fewer ozone generation plates than a secondary plate grouping. Thus, the generator includes at least four independent ozone generation control channels to energize the primary and secondary plate groupings of each of the at least two plate stacks. The number of plates in a plate grouping may optionally be altered to reduce the ozone generation capacity of the primary plate grouping in relation to the secondary plate grouping through the movement of insulators between the stacked ozone generation plates.

The at least four independent ozone generation control channels provide redundancy and allow for multiple modes of operation, including unoccupied and occupied living space modes in addition to interleaved operation of the independently electrically addressable plate groupings, which significantly extends the useful life of the individual ozone generation plate groupings.

Neither is an active ozone decomposer, such as an appropriate wavelength ultraviolet (UV) light, necessary to reduce generated ozone levels within the living space. Preferably, the ozone levels are monitored in the living space, so appropriate levels are maintained. Thus, while an active ozone decomposer may be used to decompose undesired ozone levels, it is not preferred.

Figure 1:
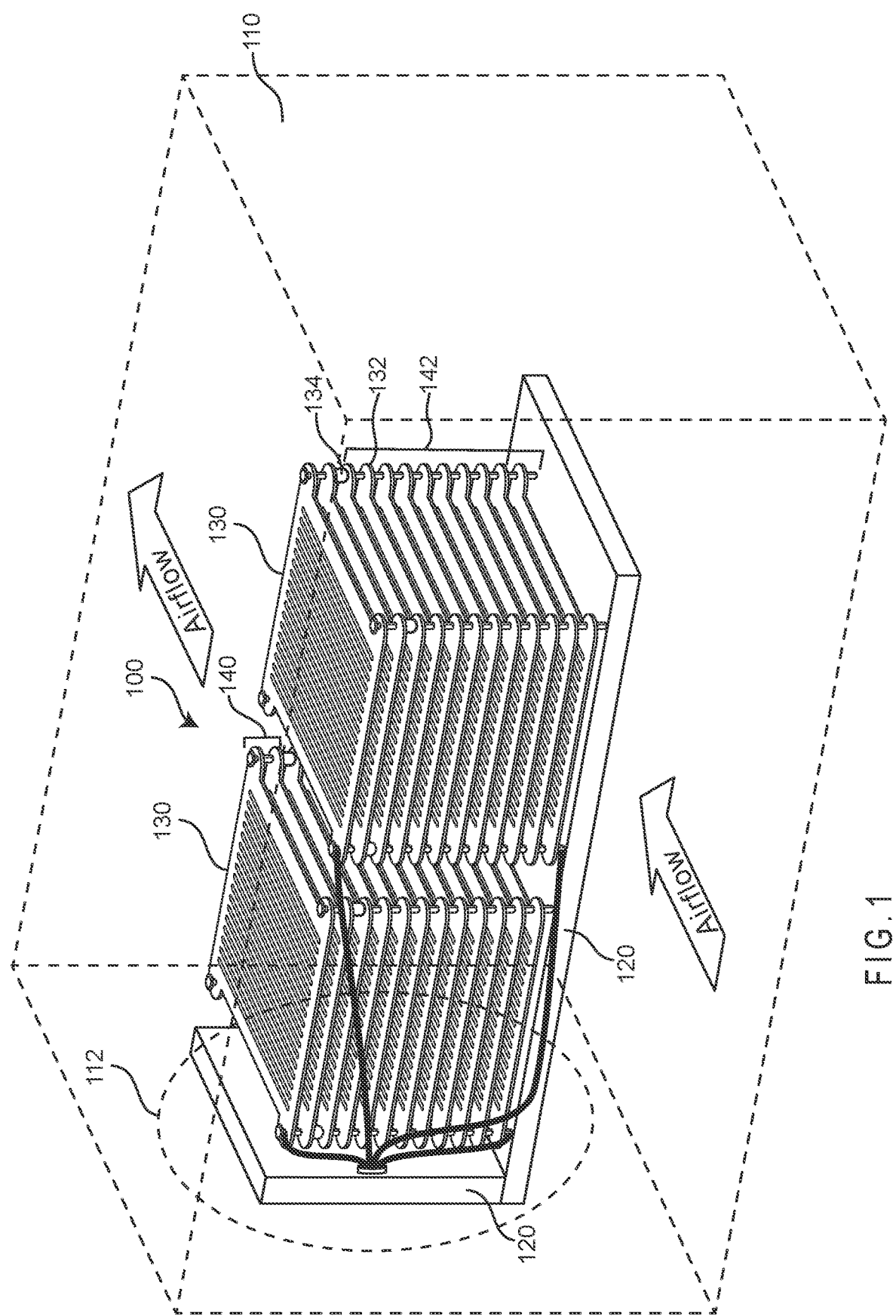
FIG. 1 represents components of an HVAC ozone generator inserted into the return airflow of an HVAC system by installing the generator through a hole cut in a side of HVAC system return duct.

FIG. 1 represents components of an HVAC ozone generator 100 inserted into the return airflow of an HVAC system by installing the generator 100 through a hole 112 cut in a side of HVAC system return duct 110. The generator 100 is positioned within the duct 110 preferably to maximize airflow across and through the generator 100. In the figure, in response to a HVAC system fan (not shown) being turned on, air is represented as flowing through the "front" opening of the duct 110 and exiting out the "rear" of the duct 110 after passing through the generator 100. As the generator 100 is positioned within the duct 110, the generator 100 does not require an air movement device, such as motors, fans, pumps, or the like to generate airflow through the generator 100. Preferably, the generator 100 is sized to reside within at least 60% of a cross-sectional area of the duct 110.

The generator 100 is preferably placed in the return ducting that provides airflow to the temperature modification system, but also may be placed in the supply ducting that provides airflow to the living space. However, this reduces the ozone levels around the components of the HVAC temperature modification system, which is less desired as the temperature modification system is often the greatest source of undesirable bacterial growth in an HVAC system. Furthermore, the cooling and thus energy efficiency of the HVAC system may be improved by reducing the bacterial growth that results in dust entrapment and reduced airflow through the temperature modification system.

The generator 100 includes a base 120 that supports at least two ozone generation plate stacks 130 within the interior of the return duct 110. While two of the plate stacks 130 are represented in the figure, additional plate stacks may be added to the base 120. Each of the plate stacks 130 includes at least three, and preferably more, ozone generation plates 132. Each of the plate stacks 130 includes electrical insulators 134 that electrically separate a primary plate grouping 140 of one or more plates from a secondary plate grouping 142 of two or more plates. Each of the plate stacks 130 is actuated by at least two independent ozone generation control channels (not shown), with each control channel energizing a plate grouping.

Preferably, and as represented in the figure, the primary plate grouping 140 includes fewer of the ozone generation plates 132 than the secondary plate grouping 142. In the figure, the primary plate grouping 140 includes two of the ozone generation plates 132, while the secondary plate grouping 142 includes ten of the ozone generation plates 132. While each of the ozone generation control channels actuates at least one of the ozone generation plates 132, a desired ozone concentration per unit time may be provided by moving the electrical insulators 134 to add or subtract one or more of the ozone generation plates 132 from a specific plate grouping, as will be discussed further below.

By providing at least two of the plate stacks 130, with each of the plate stacks 130 including at least primary and secondary plate groupings 140, 142, respectively, the generator 100 provides redundancy. If either the primary or the secondary ozone generation control channel and/or plate grouping fails for a first plate stack, the corresponding primary or secondary control channel and/or plate grouping from a second plate stack can be substituted to operationally replace the failed primary or secondary control channel and/or plate grouping from the first plate stack.

The at least two of the plate stacks 130 also provide for interleaved operation of the control channels, thus substantially reducing the likelihood of failure, as will be discussed further below. By providing the primary plate grouping 140 with fewer ozone generation plates than the secondary plate grouping 142, the primary control channel of any primary plate grouping may be used when a living space is occupied, while the secondary control channel of any secondary plate grouping may be used when the living space is vacant and higher ozone concentrations in the living space is desired.

Figure 2:
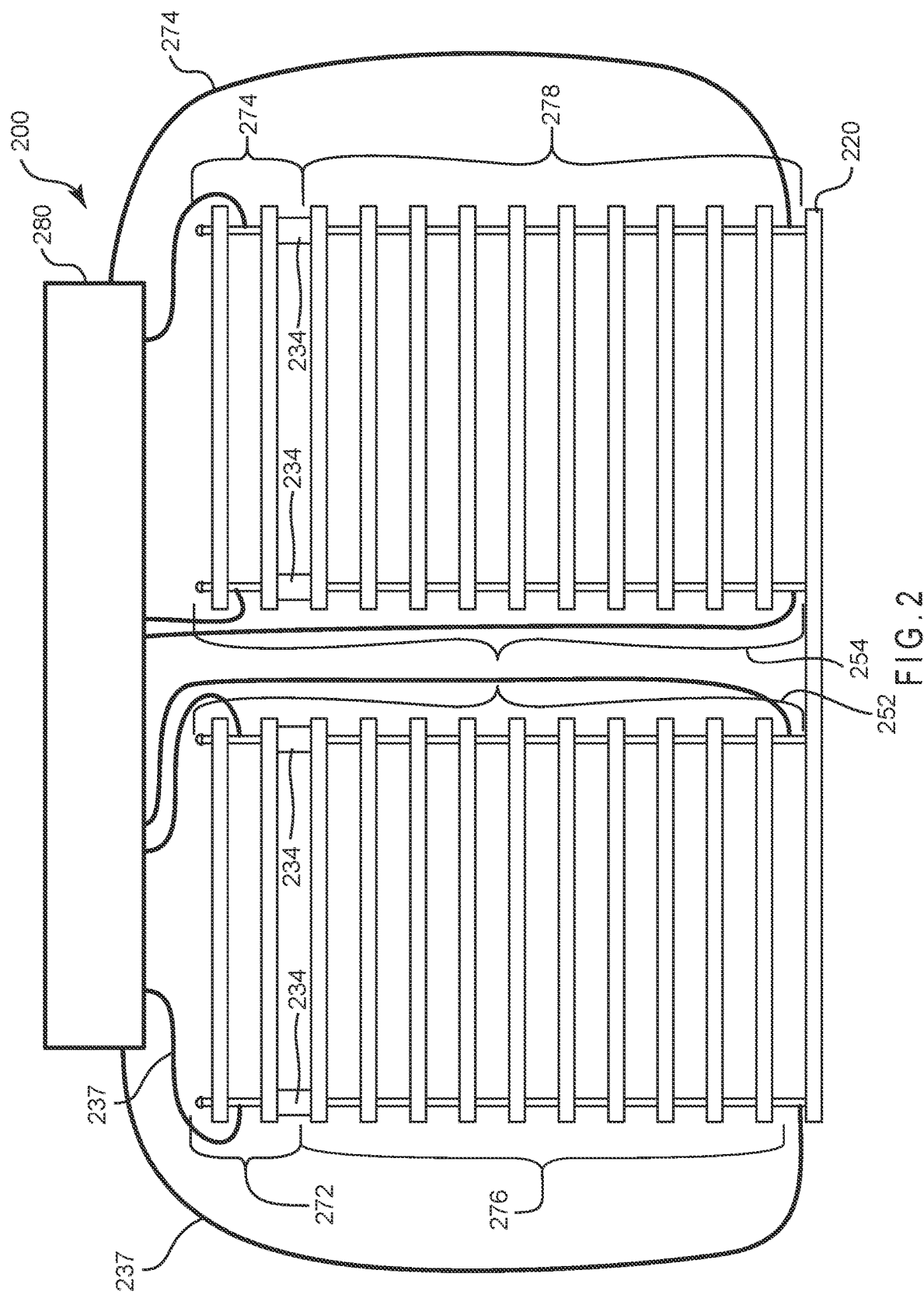
FIG. 2 represents components of an HVAC ozone generator including first plate stack and second plate stack, with an associated energizer providing at least four, independent ozone generation control channels.

FIG. 2 represents components of an HVAC ozone generator 200 including first plate stack 252 and second plate stack 254, with an associated energizer 280 providing at least four, independent ozone generation control channels. The first plate stack 252 includes independently electrically addressable primary plate grouping 272 and independently electrically addressable secondary plate grouping 276. The second plate stack 254 includes independently electrically addressable primary plate grouping 274 and independently electrically addressable secondary plate grouping 278. The at least four independently electrically addressable plate groupings 272, 274, 276, 278 are independently controllable by the at least four, independent ozone generation control channels as implemented via the energizer 280.

By independently controllable it is meant that any one or more of the independently electrically addressable plate groupings 272, 274, 276, 278 may be turned on or off respective of the other plate groupings by the energizer 280. Thus, if the desired ozone output from the ozone generator 200 is not achieved with an individual plate grouping, for example the first plate stack plate grouping 272, additional plate groupings may be energized.

While it is possible due to the at least four independent control channels to simultaneously energize all four plate groupings, to maintain redundancy and system life with interleaving, preferably a singular plate grouping, whether primary or secondary, is energized at any one time. Thus, there are at least four independent ozone generation control channels within the energizer 280.

As represented in the figure, each of the plate stacks 252, 254 includes twelve individual plates split into a two-plate primary grouping, such as the primary plate grouping 272, and a ten-plate secondary grouping, such as the secondary plate grouping 276. Electrically separating the primary plate grouping 272 from the secondary plate grouping 276 are insulators 234. The insulators 234 define the number of ozone generation plates in each plate grouping.

As the energizing wires originating from the energizer 280 electrically communicate with the top and bottom of the plate stack 252, by moving the insulators 234 to separate the third and fourth plates down from the top of the first plate stack 252 (as opposed to the depicted second and third plate division), the primary plate grouping 272 can be converted to include three plates (as opposed to the depicted two) while the secondary plate grouping 276 is converted to include nine plates (as opposed to the depicted ten). This movement of the insulators 234 would increase the ozone available from the primary plate grouping 272 in relation to the secondary plate grouping 276. The movement of the insulators 234 may include altering the voltage and/or amperage capacity of the energizer 280 as a different energizer output capacity may be desired for plate stacks having a different number of plates.

As the primary plate grouping 272 is used by the generator 200 when the room is occupied, by increasing the primary plate grouping 272 from two to three plates, the generator 200 has thus been reconfigured to provide the desired occupied living space mode ozone level in a larger room volume. Similarly, by moving the insulators 234 "up" between the first and second plates, the generator 200 may be configured to provide occupied living space mode ozone levels in a smaller room volume. While these changes are described in the context of the first plate stack 252, in practice they also would be implemented for the second plate stack 254 to maintain redundancy and interleave capability. Thus, one may reconfigure the ozone generated by any of the plate groupings by moving the insulators 234. This allows the ozone output of the primary control channel and associated plate grouping to be "tuned" to a specific living space volume both before and after installation of the generator 200 in the HVAC system ducting if more or less ozone is needed in view of the desired occupied mode ozone concentration thresholds, as discussed further below.

By interleaving, it is meant than when operating in occupied living space mode for example, the primary plate grouping 272 is energized for the desired time. Then, after the desired pause, the primary plate grouping 274 is energized for the desired time. Then, after the desired pause, the primary plate grouping 272 is again energized for the desired time, and so on. Similarly, interleaving for an unoccupied living space mode may be implemented by energizing secondary plate groupings 276 and 278 in the described alternating manner.

Figure 3:
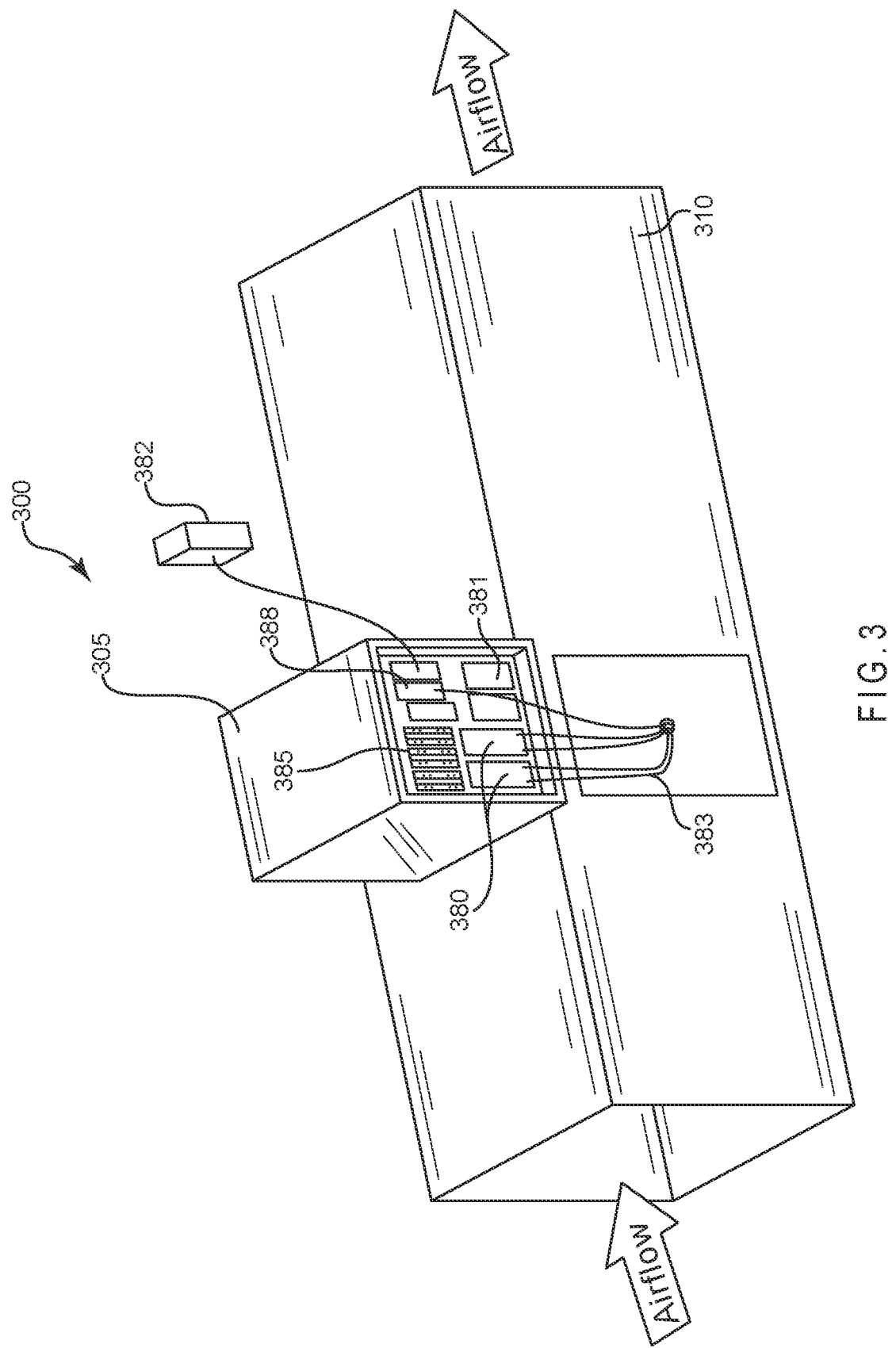
FIG. 3 represents an HVAC ozone generator system including energizer, energizer controller, sensor electronics, airflow sensor, and ozone sensor.

Preferably, each individual ozone generation plate can produce from 200 mg to 10 grams of ozone per hour in a pure oxygen environment. Preferable individual ozone generation plates can produce at least 350 mg to at least 8 grams of ozone per hour in a pure oxygen environment. Ozone generation plates that produce approximately 350 mg, approximately 3 g, or approximately 8 mg of ozone per hour are especially preferred at present. Presently preferred ozone generation plates include the A2Z Plate #700, available from A2Z Ozone, Louisville, KY and the 1G, 5G, 8G, 16G, 40G, and 80G ceramic stainless-steel plates as available from Sihon Electronics, Co., Ltd., China FIG. 3 represents an HVAC ozone generator system 300 including energizer 380, energizer controller 385, sensor electronics 381, airflow sensor 388, and ozone sensor 382. The system 300 includes first and second plate stacks (not shown) internal to HVAC system return duct 310. In this implementation the energizer 380 includes two energizer boards, thus with an energizer board for each of the two plate stacks. However, this is not required. The energizer 380, the energizer controller 385, and the sensor electronics 381 are included in housing 305, but could be otherwise located.

Preferably, the ozone sensor 382 is remotely located in a living space and communicates with the sensor electronics 381 via wired or wireless (not shown) electrical communication. Power wires 383 establish electrical communication with the first and second plate stacks internal to the return duct 310 and the energizer boards constituting the energizer 380. As previously described in the context of FIG. 1, the plate stacks are inserted through an opening formed in a side of the return duct 310.

Figure 4:
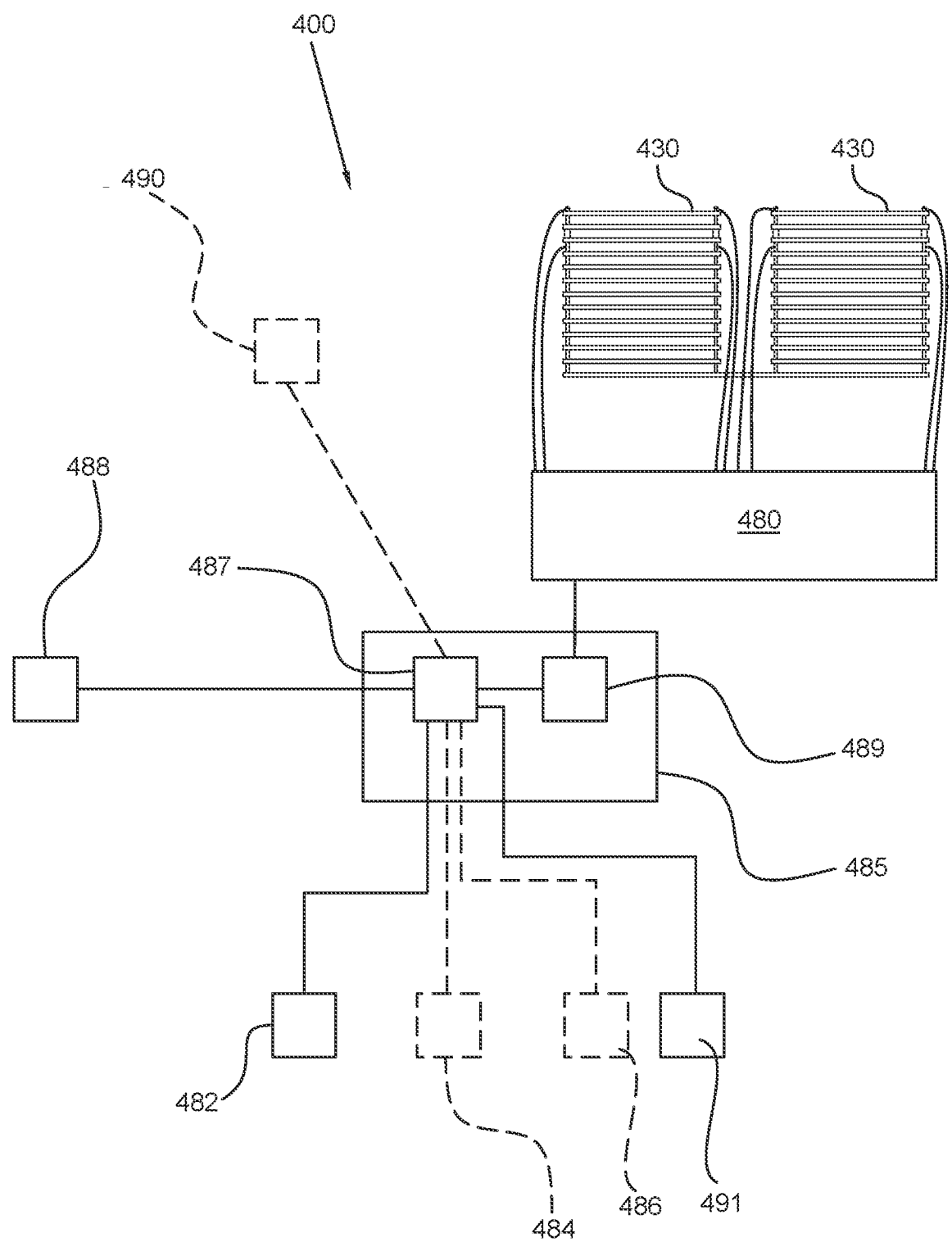
FIG. 4 represents an HVAC ozone generation system including energizer, energizer controller, ozone sensor, airflow sensor, optional temperature sensor, optional humidity sensor, presence sensor, and optional display controller.

FIG. 4 represents an HVAC ozone generation system 400 including energizer 480, energizer controller 485, ozone sensor 482, airflow sensor 488, optional temperature sensor 484, optional humidity sensor 486, living space presence sensor 491, and optional display controller 490. The optional display controller 490 may provide for user input, such as selection of living space unoccupied or occupied operation mode, and may display the operation mode and sensor levels associated with the energizer controller 485. The optional display controller 490 may provide additional information, such as if a control channel has failed, as will be discussed further below in the context of interleaved operation.

The display controller 490 may be analog or digital or both in operation. The display controller 490 may include a LCD, a LED, an OLED, a vacuum fluorescent, or other display adapted to show a numerical reading. Other display types may be used, such as when the display controller is implemented as a smartphone or other computer application. The display controller 490 may include a cellular router, or other electronics to facilitate wireless communication.

The display controller 490 electrically communicates with the energizer controller 485. The display controller 490 may be separate from the energizer controller 485, such as when the display controller 490 is in wireless communication with the energizer controller 485. Thus, the display controller 490 may be removed from the energizer controller 485, such as when the display controller 490 is implemented as a smartphone application and electrically communicates with the energizer controller 485 via a wi-fi network through the internet (not shown).

The ozone sensor 482 determines the ozone content of the air in the living space and is thus preferably placed within the living space. The ozone sensor 482 placed within the living space may be implemented with multiple sensors that provide an average or other comparative value as the ozone concentration in the living space. Preferably, the ozone sensor 482 communicates wirelessly with the energizer controller 485, but wired communication also may be used. In addition to the ozone sensor 482, an additional ozone sensor (not shown) may be placed in the ducting of the HVAC system to provide additional ozone concentration information to the energizer controller 485. Preferably, the ozone sensor 482 has a measurement range of approximately 0.05 to 20 ppm ozone in the atmosphere.

The ozone sensor 482 may be implemented to include an Eco Sensor-OS-6, Eco Sensor OEM-3, A2Z Ozone Sensor-03-100, or Spec Sensor 15×15 20 ppm 110-402, such as available from Eco Sensors, Newark, CA, A2Z, or SPEC Sensors, Newark CA, respectively. Ozone sensors from other sources may be used. Other ozone sensor types with other operating ranges other than those provided as examples may be used to determine the ozone content in the air of the living space or the ducting.

The airflow sensor 488 determines whether air is flowing through the ducting of the HVAC system. The airflow sensor 488 may be implemented as an airflow sensor mounted upstream of plate stacks 430 or elsewhere in the ducting. In another implementation, the airflow sensor 488 may sense the difference in air pressure internal to the ducting and the air outside of the ducting. The airflow sensor 488 also may be implemented as an electrical input responsive to the HVAC system fan (not shown). However, in this implementation, the system 400 is not "self-contained", as connection to the existing HVAC system is required.

The presence sensor 491 determines if the living space includes human or animal occupants. The presence sensor 491 may be of the IR type commonly used in residential security systems to detect movement, ultrasound, and the like. The presence sensor 491 is placed in the living space and may be in wired or preferably wireless communication with the energizer controller 485. The presence sensor 491 may include more than one sensing unit, such as when the living space includes multiple rooms or is relatively large.

The optional temperature sensor 484 determines the temperature of the air in the ducting and/or in the living space. The temperature may be measured using a thermistor, thermometer, other temperature sensing device, or with an input from the HVAC system. The optional temperature sensor 484 may be one or more temperature measurement devices, that may report an average or other comparative temperature value. Preferably, the temperature sensor 484 has an operational range of approximately −30° C. to 50° C. Other techniques may be used to determine the temperature of the air in the ducting and/or in the living space.

The optional humidity sensor 486 determines the humidity of the air in the ducting and/or in the living space. The optional humidity sensor 486 may be one or more humidity measurement devices, that may report an average or other comparative humidity value. Preferably, the humidity sensor 486 has a measurement range of approximately 35%-75% relative humidity in the atmosphere. The optional humidity sensor 486 may be implemented to include a Honeywell HIH-5030/5031 series low voltage humidity sensor, such as available from Honeywell, http://sensing.honeywell.com. Other humidity sensors and techniques may be used to determine the amount of moisture in the air of the ducting and/or in the living space.

The energizer controller 485 includes processor 487 and storage medium 489. The energizer controller 485 optionally may include a real-time clock with calendar capability (not shown) and other electronics to provide additional features to the energizer controller 485. The storage medium 489 may be a magnetic, optical, or semiconductor memory, another storage device, or the like. The storage medium 489 may be a fixed memory device, a removable memory device, such as a memory card, remotely accessed via wireless communication, or the like. In addition to fixed memory, the storage medium 489 may include removable memory, such as in the form of a SD card or similar removable memory device.

The processor 487 determines which of the at least four available independent ozone generation control channels to energize or turn off by supplying the appropriate instruction to the energizer 480 using the computer readable non-transient software code and data stored in the storage medium 489. The processor 487 also may store information such as sensor readings, operating times, status, and the like in the storage medium 489 for later review and interpretation. This information also may be transmitted, such as to the display controller 490 through a wired or wireless network.

The processor 487 may energize or turn off one or more of the at least four independent ozone generation control channels in response to a reading from the ozone sensor 482, the airflow sensor 488, the presence sensor 491, the optional temperature sensor 484, or the optional humidity sensor 486 in any combination. The processor 487 also may energize or turn off one or more of the at least four independent ozone generation control channels in response to user input, such as selection of an available operating mode. The processor 487 may consider the reading from one or more of the sensors and the user selected operating mode to determine which of the at least four independent ozone generation control channels to energize or turn off and for the duration of energized or off operation.

The processor 487 also may activate an alarm (not shown) if readings from one or more of the sensors is outside of a predetermined threshold or range. For example, a predetermined alarm and ozone generator shutdown threshold of 0.1 ppm ozone concentration in the living space during occupied mode may be stored in the storage medium 489. Preferably, in response to instructions stored in the storage medium 489, the processor 487 will not implement any operating mode if the airflow sensor 488 fails to report airflow through the HVAC system ducting and thus through the plate stacks 430. Preferably, in response to instructions stored in the storage medium 489, the processor 487 may deenergize or not energize unoccupied mode when the presence sensor 491 indicates that the living space is occupied.

Preferably, the computer readable non-transient software code and data stored in the storage medium 489 provides the processor 487 with at least two operating modes that may be implemented. The at least two operating modes include unoccupied and occupied modes for the living space. The computer readable non-transient software code and data stored in the storage medium 489 may provide the processor 487 with additional operating modes.

Unoccupied mode is implemented by the processor 487 after the presence sensor 491 reports that the living space is unoccupied, and it is desirable from a time-of-day perspective to have enhanced sanitization of the HVAC ducting and living space. Unoccupied mode supplies enough ozone to the HVAC ducting and living space to substantially reduce contaminants and odor causing irritants from the living space, and especially from the interior of the HVAC ducting. Preferably, unoccupied mode kills at least 70% of the contaminants and oxidizes at least 70% of odor causing substance within the living space. More preferably, unoccupied mode achieves sanitization of the living space.

In unoccupied mode, the processor 487 provides instruction through one of the at least two secondary control channels to energize a secondary plate grouping. While more than one secondary plate grouping may be energized simultaneously to provide a surge of ozone, preferably one secondary plate grouping is energized at a time to permit interleaving of the at least two secondary plate groupings and to provide secondary plate grouping redundancy in the event of a failure of a secondary control channel or plate grouping.

During unoccupied mode, a concentration from 2 to 15 ppm of ozone is generated and maintained in the living space, preferably for 15 minutes to 2 hours. Preferably, during unoccupied mode a concentration from 5 to 15 ppm ozone is generated and maintained in the living space for 15 minutes to 1 hour. More preferably, during unoccupied mode a concentration from 8 to 15 ppm ozone is generated and maintained in the living space for 15 to 30 minutes. The processor is configured to deenergize or not energize unoccupied mode if the ozone concentration in the living space exceeds the 2 to 15 ppm threshold by 20% or if the presence sensor detects people or pets in the living space.

During unoccupied mode, the ozone concentration within the HVAC system ducting reaches levels that are at least twice, preferably at least three times that of the living space, as the generator 100 is present in the ducting. Thus, ozone concentration levels from 10 to 45 ppm, preferably from 15 to 30 ppm are achieved within the HVAC system ducting during unoccupied mode. As previously mentioned, enhanced ozone concentrations within the HVAC system ducting and especially around the components of the HVAC temperature modification system provides an enhanced benefit in relation to the living space alone.

If activation of a first plate stack secondary control channel and associated secondary plate grouping does not produce the lower 2 ppm ozone concentration in the living space after a predetermined time, such as 10 to 60 minutes, preferably 15 to 30 minutes, and more preferably 25 to 35 minutes, the processor 487 deactivates the first plate stack secondary control channel, and switches to the secondary control channel of the second plate stack, as the first plate stack secondary control channel or associated plate grouping has failed. Thus, interleaving between the at least two secondary plate groupings is stopped, and the second plate stack secondary control channel and associated plate grouping is singularly used to provide unoccupied mode. Preferably, an error code is logged and reported by the processor 487.

Occupied mode is implemented by the processor 487 when people or pets are present or likely to be present in the living space. Occupied mode may be implemented before, during, or after people or pets occupy the living space. Occupied mode also may be implemented when people and pets are most likely to occupy the living space from a time-of-day perspective. Occupied mode supplies enough ozone to the living space to maintain or preferably reduce the contaminants and odors that otherwise would be brought into the living space by people and pets. The ozone level provided to the living space through the HVAC system ducting in occupied mode is less than in unoccupied mode.

In occupied mode, a single primary plate grouping is energized by a primary ozone generation control channel. While more than one primary plate grouping may be energized simultaneously to provide an increased ozone level in the living space for a relatively short time, preferably a single primary plate grouping is energized at a time to permit interleaving of the at least two primary plate groupings and to provide primary plate grouping redundancy in the event of a failure of a primary control channel or plate grouping.

During occupied mode, a concentration from 0.05 to 0.08 ppm ozone may be generated and maintained in the living space. Preferably, during occupied mode, an average concentration of 0.06 ppm ozone may be generated and maintained in the living space. The ozone sensor 482 provided in the living space is used to ensure that ozone levels within the living space do not exceed by more than 25% the 0.08 ppm ozone concentration. Furthermore, the at least two primary plate groupings preferably may each be configured by selecting the insulator positioning of the plate stack to not exceed the 0.08 ppm ozone concentration by more than 25% in the living space when energized. Thus, in addition to feedback control of maximum living space ozone concentration via the ozone sensor 482, the insulator positioning of the plate stack may be chosen so it is impossible for either of the at least two primary plate groupings to produce undesired ozone levels in the living space when energized.

During occupied mode, the ozone concentration within the HVAC system ducting reaches levels that are at least twice, preferably at least three times that of the living space, as the generator 100 is present in the ducting. Thus, ozone concentration levels from 0.1 to 0.24 ppm, preferably from 0.15 to 0.18 ppm are achieved within the HVAC system ducting during occupied mode. As previously mentioned, enhanced ozone concentrations within the HVAC system ducting and especially around the components of the HVAC temperature modification system provides an enhanced benefit in relation to the living space alone.

If activation of a first plate stack primary control channel and associated primary plate grouping does not produce the lower 0.05 ppm ozone concentration in the living space after a predetermined time, such as 10 to 60 minutes, preferably 15 to 45 minutes, and more preferably 25 to 35 minutes, the processor 487 deactivates the first plate stack primary control channel, and switches to the primary control channel of the second plate stack, as the first plate stack primary control channel or associated plate grouping has failed. Thus, interleaving is stopped, and the second plate stack primary control channel and associated plate grouping is singularly used to provide occupied mode. Preferably, an error code is logged and reported by the processor 487.

During occupied mode, the processor 487 preferably interleaves energized operation of the at least two primary control channels and associated plate groupings to prolong the life of the ozone generation plates. Thus, to maintain the ozone level in the living space as provided by a single primary control channel and plate grouping, the processor 487 can consecutively energize and then turn off each primary control channel for a set time period, such as approximately 15 minutes. In this way, to provide an hour of continuous occupied mode operation, each of the at least two primary control channels is energized for a total of approximately 30 minutes. If more than two primary control channels and associated primary plate groupings are available, the operation of each ozone generation control channel on an hourly basis may further be reduced to prolong the life of the ozone generation plates. Through this interleaved operation, the duty cycle of individual primary plate groupings is reduced to approximately one-half of what it would be if a single plate stack were used. As ozone generation plates have a finite lifespan, the useful life of the ozone generator substantially increases.

Interleaved operation also may be implemented during unoccupied mode as at least two secondary control channels and associated plate groupings are available for interleaving. Thus, as previously discussed in the context of occupied mode, of the at least two available secondary control channels and associated plate groupings, only one of the at least two secondary plate grouping is preferably energized at a time during unoccupied mode.

To provide a clear and more consistent understanding of the specification and claims of this application, the following definitions are provided.

Bacteria includes, but is not limited to, Salmonella enteritidis, *E. coli* 0157:H7, *Listeria monocytogenes*, *Shigella dysenteriae*, *Micrococcus aureus*, *Clostriduim botulinum*, *Mycobacterium tuberculosis*, *Bacillus anthracis*, and *Streptococcus* sp.

Mold includes, but is not limited to, *Botrytis*, *Rhizopus*, *Penicillium*, and *Aspergillus*.

Substantially reduce in the context of microorganism reduction means that at least 70% of the previously living bacteria, viruses, fungus, or mold is killed. Higher kill rates, such as what is referred to as a three (99.9%) to four (99.99%) log reduction or "kill" are preferred. A three-log reduction may be referred to as sanitize or sanitizing, while a four-log reduction may be referred to as disinfect or disinfecting. The terms sterilize and sterilization are often used in the context of a six-log-plus (99.9999+) reduction.

Electrical communication means either wired or wireless.

Unless otherwise indicated, all numbers expressing quantities of ozone used or times in the specification and claims are to be understood as indicating both the exact values as shown and as being modified by the term "about". Thus, unless indicated to the contrary, the numerical values of the specification and claims are approximations that may vary depending on the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

Unless the context clearly dictates otherwise, where a range of values is provided, each intervening value to the tenth of the unit of the lower limit between the lower limit and the upper limit of the range is included in the range of values.

Spatially relative terms, such as "up," "down," "right," "left," "beneath," "below," "lower," "above," "upper" and the like, may be used for ease of description to describe one element or feature's relationship to another element(s) or feature(s) as illustrated in the figures. Spatially relative terms are intended to encompass different orientations of the device in use or operation in addition to the orientation depicted in the figures. For example, if the device in the figures is turned over or rotated, elements described as "below", or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

The simplified diagrams and drawings do not illustrate all the various connections and assemblies of the various components, however, those skilled in the art will understand how to implement such connections and assemblies, based on the illustrated components, figures, and provided descriptions.

What is claimed is:

1. A HVAC duct ozone generator, for reducing contamination of a HVAC system duct and associated living space, the HVAC system duct ozone generator comprising:
   at least two ozone generator plate stacks comprising a first ozone generator plate stack and a second ozone generator plate stack,
     where the first ozone generator plate stack comprises at least two first plate stack independently electrically addressable plate groupings and the second ozone generator plate stack comprises at least two second plate stack independently electrically addressable plate groupings,
     where the independently electrically addressable plate groupings are independently controllable by independent ozone generation control channels implemented via an energizer, where the energizer is configured to turn on or off one or more of the independently electrically addressable plate groupings respective of the other plate groupings, where a primary plate grouping of the first plate stack comprises fewer ozone generator plates than a secondary plate grouping of the first plate stack, and where a primary plate grouping of the second plate stack comprises fewer ozone generator plates than a secondary plate grouping of the second plate stack where the primary plate grouping of the first plate stack is electrically insulated from the secondary plate grouping of the first plate stack with first plate stack insulators, where the first plate stack insulators are movable to change a number of the ozone generator plates in the primary plate grouping versus the secondary plate grouping of the first plate stack, where the primary plate grouping of the second plate stack is electrically insulated from the secondary plate grouping of the second plate stack with second plate stack insulators, and where the second plate stack insulators are movable to change a number of the ozone generator plates in the primary plate grouping versus the secondary plate grouping of the second plate stack.

2. The generator of claim 1, the independent ozone generator control channels are in electrical communication with and configured to energize the primary plate grouping of the first plate stack, the secondary plate grouping of the first plate stack, the primary plate grouping of the second plate stack, and the secondary plate grouping of the second plate stack.

3. The generator of claim 1, where the first plate stack insulators alter the ozone generation capacity of the primary plate grouping in relation to the secondary plate grouping of the first plate stack, and where the second plate stack insulators alter the ozone generation capacity of the primary plate grouping in relation to the secondary plate grouping of the second plate stack.

4. The generator of claim 2, where the independent ozone generator control channels are configured to provide redundancy to the primary plate grouping of the first plate stack with the primary plate grouping of the second plate stack and to provide redundancy to the secondary plate grouping of the first plate stack with the secondary plate grouping of the second plate stack.

5. The generator of claim 2, where the independent ozone generator control channels are configured to provide interleaved operation to the primary plate grouping of the first plate stack with the primary plate grouping of the second plate stack and to provide interleaved operation to the secondary plate grouping of the first plate stack with the secondary plate grouping of the second plate stack.

6. The generator of claim 1 lacking an active ozone decomposer.

7. The generator of claim 1 positioned within the return airflow of a HVAC system.

8. The generator of claim 1 configured to reside within at least 60% of a cross-sectional area of the HVAC system duct.

9. The generator of claim 1, where the first plate stack includes at least three ozone generation plates and the second plate stack includes at least three ozone generation plates.

10. The generator of claim 9, where each of the at least three ozone generation plates generates from 200 mg to 10 grams of ozone per hour in a pure oxygen environment.

11. The generator of claim 1, where the primary plate grouping of the first plate stack and the primary plate grouping of the second plate stack are configured to generate the same ozone concentration per unit time, and where the secondary plate grouping of the first plate stack and the secondary plate grouping of the second plate stack are configured to generate the same ozone concentration per unit time.

12. The generator of claim 2, further comprising at least one ozone sensor in electrical communication with the four independent ozone generator control channels through an energizer controller.

13. The generator of claim 2, further comprising at least one living space presence sensor in electrical communication with the independent ozone generator control channels through an energizer controller.

14. The generator of claim 2, further comprising a display controller and an energizer controller in electrical communication with the independent ozone generator control channels.

15. The generator of claim 14, where the display controller is in wireless electrical communication with the energizer controller.

16. The generator of claim 14, where the energizer controller is responsive to the display controller and where the display controller provides for user input.

17. The generator of claim 14, where the energizer controller is responsive to electrical communication with a remote computing device configured to allow remote control of the energizer controller.

18. The generator of claim 14, where the energizer controller includes a processor and a storage medium.

19. The generator of claim 18, where the processor stores sensor readings and operating times on the storage medium.

20. The generator of claim 1, where the primary plate grouping of the first plate stack and the primary plate grouping of the second plate stack are configured to not provide greater than 0.1 ppm ozone to the living space during operation of the generator.

21. The generator of claim 1, where the secondary plate grouping of the first plate stack and the secondary plate grouping of the second plate stack are configured to generate sufficient ozone to kill at least 70% of the contaminants and to oxidize at least 70% of the odor causing substance within the living space.

22. The generator of claim 1, where the secondary plate grouping of the first plate stack and the secondary plate grouping of the second plate stack are configured to generate and maintain a concentration from 2 to 15 ppm of ozone in the living space for a duration of 15 minutes to 2 hours.

23. The generator of claim 1, where the secondary plate grouping of the first plate stack and the secondary plate grouping of the second plate stack are configured to generate a concentration from 15 to 45 ppm of ozone in the HVAC system duct.

24. The generator of claim 1, where the primary plate grouping of the first plate stack and the primary plate grouping of the second plate stack are configured to generate and maintain a concentration from 0.05 to 0.08 ppm of ozone in the living space while the living space is occupied.

25. The generator of claim 1, where the primary plate grouping of the first plate stack and the primary plate grouping of the second plate stack are configured to generate a concentration from 0.1 to 0.24 ppm of ozone in the HVAC system duct.

* * * * *